(12) United States Patent
Clerivet

(10) Patent No.: US 10,416,014 B2
(45) Date of Patent: Sep. 17, 2019

(54) DEVICE FOR DETECTING AIR FLOWS

(71) Applicant: SIEMENS SCHWEIZ AG, Zurich (CH)

(72) Inventor: Pierre Clerivet, Guyancourt (FR)

(73) Assignee: Siemens Schweiz AG, Zurich (CH)

( * ) Notice: Subject to any disclaimer, the term of this patent is extended or adjusted under 35 U.S.C. 154(b) by 134 days.

(21) Appl. No.: 15/516,455

(22) PCT Filed: Sep. 3, 2015

(86) PCT No.: PCT/EP2015/070113
§ 371 (c)(1),
(2) Date: Apr. 3, 2017

(87) PCT Pub. No.: WO2016/050443
PCT Pub. Date: Apr. 7, 2016

(65) Prior Publication Data
US 2018/0202848 A1     Jul. 19, 2018

(30) Foreign Application Priority Data

Oct. 1, 2014    (EP) ..................................... 14290296

(51) Int. Cl.
*G01F 1/698*       (2006.01)
*G01F 1/684*       (2006.01)
*G01N 25/18*       (2006.01)
*G01F 1/68*        (2006.01)
*G01F 1/69*        (2006.01)

(52) U.S. Cl.
CPC .............. *G01F 1/6986* (2013.01); *G01F 1/68* (2013.01); *G01F 1/684* (2013.01); *G01F 1/69* (2013.01); *G01N 25/18* (2013.01)

(58) Field of Classification Search
CPC ..................................................... G01F 1/6986
See application file for complete search history.

(56) References Cited

U.S. PATENT DOCUMENTS

| 3,803,913 | A | | 4/1974 | Tracer | |
|---|---|---|---|---|---|
| 4,581,930 | A | * | 4/1986 | Komons | ................. G01F 1/696 73/204.17 |
| 5,031,126 | A | * | 7/1991 | McCulloch | ............. G01F 1/698 340/622 |
| 5,033,299 | A | | 7/1991 | Tanaka et al. | |
| 5,685,194 | A | * | 11/1997 | McCulloch | ............. G01F 1/696 73/204.11 |
| 6,435,023 | B1 | | 8/2002 | Kobayashi et al. | |

(Continued)

FOREIGN PATENT DOCUMENTS

| CN | 1163394 A | 10/1997 |
|---|---|---|
| CN | 1573301 A | 2/2005 |

(Continued)

*Primary Examiner* — Daniel S Larkin
*Assistant Examiner* — Anthony W Megna Fuentes
(74) *Attorney, Agent, or Firm* — Laurence Greenberg; Werner Stemer; Ralph Locher

(57) ABSTRACT

A device for detecting air flows includes an air line channeling an air flow. The line (for example a tube) includes at least one first temperature sensor and one second temperature sensor (inside the tube). At least one of the sensors is subjected to periodic temperature fluctuations controlled by at least one heating device, such as a variable-current power source dedicated to the sensor.

5 Claims, 1 Drawing Sheet

(56) References Cited

U.S. PATENT DOCUMENTS 7,137,298 B2  11/2006  Matsumoto et al.
2013/0025364 A1  1/2013  Bach

FOREIGN PATENT DOCUMENTS

FR  2983950 A1  6/2013
GB  2482004 A   1/2012
JP  H0244211 A  2/1990

* cited by examiner

M1=Smon1 + Smon2
M2=Smeas

DEVICE FOR DETECTING AIR FLOWS

BACKGROUND OF THE INVENTION

Field of the Invention

The present invention relates to a device for detecting air flows including an air line channeling the air flow. The air line includes at least one first temperature sensor and one second temperature sensor.

There are a range of devices available that are designed to detect the presence of an air flow or to measure an air flow or fluid flow in a line, such as a smoke/heat exhaust line.

In particular, it is known that it is possible to detect an air flow in a line channeling said flow using at least one temperature sensor, such as a resistive NTC temperature sensor.

Such a system is described in document FR2983950A1, the introduction to which describes a device referred to as a "thermal flow meter" for detecting the flow of a fluid in a line (such as the admission inlet of a heating device), said line including at least a first temperature sensor and a second temperature sensor (both resistive NTC temperature sensors) immersed in the fluid. One of the sensors is used to measure the temperature of the incoming fluid, and the other sensor is powered by an electrical current of known intensity, such that the temperature of same is raised above the temperature of the fluid to be measured/detected. The same document then describes an advantageous positioning solution for said sensors at a given incline in relation to a main axis of the air line or fluid line to ensure that dirt does not hinder detection of the air flow.

Depending on the choice of electrically powered temperature sensor (or heat sensor), the device for detecting air flows may require a suitable electricity supply, and consequently the energy consumption of the two sensors is quite significant. The operating cost of the device for detecting air flows is therefore also quite significant. These drawbacks make use of such a device for detecting air flows particularly unsuited for more demanding line environments, such as in onboard systems (trains, planes, etc.) or in complex infrastructure (buildings, factories, etc.).

Finally, for safety reasons, it is essential that the device for detecting air flows including at least one temperature sensor powered by an electrical current to raise the temperature of same to a given level (as in document FR2983950A1) can be checked to determine whether said sensor is subject to ageing or has suffered a failure. This also applies to the second sensor (as in document FR2983950A1) used to measure the temperature of the incoming fluid. This diagnostic check should also be cheap and draw little power. This would improve assessment of the precision of air flow detection, in particular for safety applications (for example in relation to ventilation lines used in connection with smoke/fire hazards).

SUMMARY OF THE INVENTION

One objective of the present invention is to propose a device for detecting air flows, comprising an air line channeling the air flow, said line comprising at least one first temperature sensor and one second temperature sensor, the power consumption of which is low, while ensuring safe operation.

The following is a device provided to this effect.

On the basis of a device for detecting air flows comprising an air line channeling the air flow, said line (for example a tube) comprising (inside the tube) at least one first temperature sensor and one second temperature sensor, the device according to the invention specifies that at least one of the sensors be subjected to periodic temperature fluctuations controlled by at least one heating means, such as a variable-current power source dedicated to said sensor.

Advantageously, the powered temperature sensor no longer needs to be powered continuously to increase the temperature of same to above the temperature of the air in the line (as described in the prior art document FR2983950A1). It is sufficient to ensure that the temperature of said sensor is increased in the form of a peak or plateau of short duration before a measurement (after the temperature peak/plateau) is taken by a temperature measurement module of said sensor, thereby indicating the presence or absence of an air flow in the line.

A set of sub-claims also sets out the advantages of the invention.

BRIEF DESCRIPTION OF THE SEVERAL VIEWS OF THE DRAWING

Exemplary embodiments and applications are provided using the figures described.

DESCRIPTION OF THE INVENTION

Figure 1:
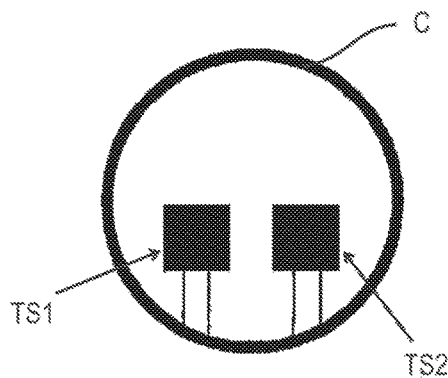
FIG. 1 is a basic diagram of two temperature sensors in a line.

FIG. 1 is a basic diagram of two temperature sensors TS1, TS2 arranged inside a line (C), which is in this case cylindrical (shown in cross section). Each of the two sensors has at least one electricity input and one measurement output, these inputs and outputs ideally being coupled outside the line to control (command, monitoring) and measurement components of the device for detecting air flows.

Figure 2:
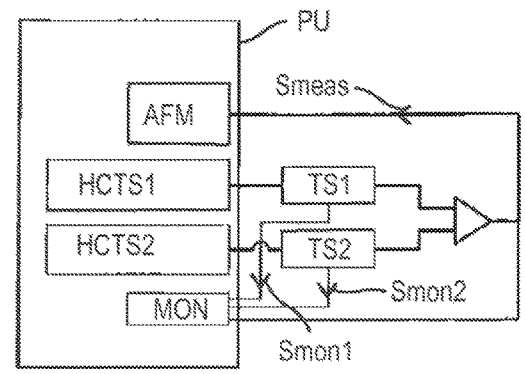
FIG. 2 is a block diagram showing the air flow detection according to the invention.

FIG. 2 shows a block diagram of the device for detecting air flows according to the invention, showing the control (command, monitoring) and measurement functions of said device.

A first measurement assembly includes the two sensors (TS1, TS2) from which at least one shared temperature measurement output (Smeas) is sent to a second assembly (PU) comprising a temperature measurement module designed to deliver an air flow measurement (AFM) or detection signal. The measurement signal Smeas is in this example a differential (amplified) signal between the two temperatures measured by the sensors TS1, TS2. The second assembly (PU) also includes monitoring means (MON) coupled respectively to each of the two outputs of the sensors, delivering two temperature signals Smon1, Smon2 respectively thereto and thereby enabling an ideally periodic safety check of each of the sensors. Finally, the second assembly (PU) also includes at least one and possibly two heating modules (HCTS1, HCTS2) coupled respectively to each of the electrical power (current) inputs of the sensors (TS1, TS2). The two heating modules enable generation of the periodic temperature fluctuations of at least one and possibly both sensors, ideally by current plateau or peak.

Figure 3:
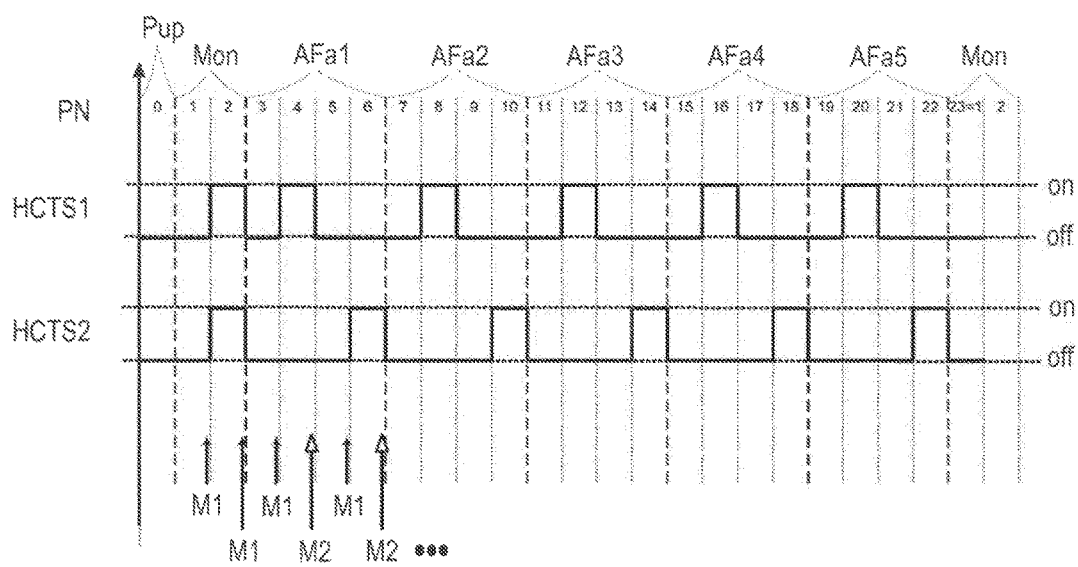
FIG. 3 is an operating diagram of the device for detecting air flows according to the invention.

Finally, FIG. 3 shows a possible example operating diagram of the device for detecting air flows according to the invention, in relation to FIGS. 1 and 2.

The X axis of the diagram shows the time component, in particular by means of a model series of successive phases (PN) indicated here cyclically between 0 and 22 phases, then 1 and 22, etc. Said phases are organized into successive subgroups (Mon, AFa1, AFa2, AFa3, AFa4, AFa5, etc.) in which:

the first is a cycle (Mon) including monitoring time points (M1 associated with signals Smon1 and Smon2) by measuring reference signals (Smon1, Smon2) and the following five cycles (AFa1, AFa2, AFa3, AFa4, AFa5, etc.) are monitoring cycles (M1) (monitoring signals) also including time measurement points (M2 associated with the signal Smeas for detecting flows).

At the beginning (PN=0) of at least the first start-up series of the device according to the invention, the first phase PN=0 corresponds to a powering-up of the sensors, providing same with a basic reference current (as low as possible).

Shortly after the two first phases PN=0 and 1, a second active phase PN=2 is triggered, switching the power to the two respective heating means HCTS1, HCTS2 to on for a limited duration in phase PN=2 (such as approximately one minute), then switching back to off so that the sensors TS1, TS2 reach the target temperature simultaneously. A first monitoring measurement (M1) of the signals Smon1, Smon2 is taken as part of a first reference measurement of the temperatures reached by the sensors.

At the end of phase PN=2, the heating means having been turned off, the temperature of the sensors should then drop according to a known cooling profile. A second monitoring measurement (M1) of the signals (Smon1, Smon2) is taken following deactivation of the heating means such that a second reference monitoring of the actual temperatures of the sensors may be undertaken at this time, following start-up of the detection device (PN=0, 1, 2).

From phase PN=3 and if no safety alert has arisen from the previous monitoring, the first cycle (subgroup AFa1) can begin, extending from phase PN=3 to phase PN=6.

At the beginning of phase PN=4, a first of the sensors is subjected to a new temperature fluctuation (high) by turning the respective heating means HCTS1 or HCTS2 on. At the end of phase PN=4, a first measurement (M2) of the signal (Smeas) is taken as part of a reference measurement of the temperature reached by the first sensor in question, indicating whether an air flow has been detected. At the beginning of the following phase PN=5, the heating means is turned off and, at the end of phase PN=5, a monitoring point (M1) is effected in order to check the correct operation of the first of the sensors subjected to a temperature increase.

Finally, at the end of phase PN=5 and at the beginning of phase PN=6, the final phase of the first cycle (subgroup AFa1), the second of the sensors is subjected to a new temperature fluctuation (high) by turning the respective heating means HCTS1 or HCTS2 on. A second measurement (M2) of the signal (Smeas) is taken as part of a reference measurement of the temperature reached by said second sensor in question, indicating whether an air flow has been detected. At the end of phase PN=6, the heating means is turned off and, at the end of the following phase PN=7, a monitoring point (M1) is effected in order to check the correct operation of the second of the sensors subjected to a temperature increase. The other cycles (subgroup AFa2, AFa3, etc.) succeeding the first cycle (AFa1) described above between phases PN=3 and 6, are performed using a control mode for the monitoring and heating means that is identical to the cycle described (AFa1).

The example diagram shown in FIG. 3 is based on two sensors and the respective heating means of same, although a simpler possible embodiment could include just one of the two sensors being subjected to periodic temperature fluctuations controlled by a single heating means (HCTS1 or HCTS2). The embodiment with two sensors and two heating means (at least each of the sensors undergoes temperature fluctuations by means of periodic temperature plateaus or peaks) is a preferred embodiment since it provides more reliable detection on account of the redundancy in the control means (sensor heating means) and temperature measurement means (sensors). Principally, the device according to the invention in which each of the sensors is subjected to temperature fluctuations controlled by at least one heating means constitutes an excellent safety device, and the fact that the sensors only require periodic and sporadic current supply by means of peaks/plateaus makes the device economical in terms of energy consumption.

Preferably, it is then also possible to provide a device in which at least one control mode of the heating means can be activated to generate temperature fluctuations comprising a simultaneous temperature increase in the two sensors (i.e. in the form of periodic temperature peaks/plateaus). Energy savings are not hugely increased in this case, but comparisons of ageing between sensors or failures in one of the sensors may be more accentuated, as a secondary objective.

It is nonetheless clear that the solution according to FIG. 3 provides better energy economy for a device according to the invention in which at least one control mode of the heating means can be activated to generate temperature fluctuations comprising temperature increases in the two sensors that alternate over time (i.e. in the form of periodic temperature peaks/plateaus). This means that the consumption of the detection device in which the sensors are activated alternatively matches the consumption of a device with a single sensor active over a long duration. Furthermore, the service life of each of the two sensors is doubled, bearing in mind that they are used half as much as a single sensor in a device with just one active sensor.

Ideally, the device according to the invention states that the temperature sensors are self-heating, said heating ideally being obtained by means of the Joule effect by injecting current into the sensor. Such heating means are particularly economical, preferably using silicon heat sensors (TI LM335A or ST LM335A), which are comparable to Zener diodes thus "improved".

Finally, in order to make the device according to the invention even more robust (redundant/safe), to increase the "reliable" service life of the sensors and/or to increase the measurement frequency, the device provides for more than two sensors to be used and to be commanded/controlled/inspected (monitoring) in the same manner as the two sensors in FIGS. 1 to 3.

The invention claimed is:
1. A device for detecting air flows, the device comprising:
an air line channeling an air flow;
at least one first temperature sensor and one second temperature sensor disposed in said air line; and
a heating device subjecting each of said temperature sensors to controlled temperature fluctuations, said heating device having at least one control mode generating the temperature fluctuations including temperature increases in said first and second temperature sensors alternating over time and said heating device being periodically switched on and off during said at least one control mode causing said sensors to be only periodically, sporadically and alternately supplied with current for increasing temperature.
2. The device according to claim 1, wherein said temperature sensors are self-heating.

3. The device according to claim 2, wherein said temperature sensors are heated by current injection.

4. The device according to claim 1, wherein said at least one first temperature sensor and one second temperature sensor include more than two sensors.

5. The device according to claim 1, which further comprises another heating device, each of said heating devices subjecting a respective one of said temperature sensors to controlled temperature fluctuations.

* * * * *